United States Patent [19]
Saifi

[11] Patent Number: 5,797,945
[45] Date of Patent: Aug. 25, 1998

[54] HEMOSTATIC DILATOR

[76] Inventor: Marwan Saifi, 15 N. Avon Dr., Claymont, Del. 19703

[21] Appl. No.: 804,834

[22] Filed: Feb. 24, 1997

[51] Int. Cl.$^6$ .................................................. A61B 17/00
[52] U.S. Cl. .................................... 606/187; 606/133
[58] Field of Search .................... 606/187, 133

[56] References Cited

U.S. PATENT DOCUMENTS

| | | | |
|---|---|---|---|
| 3,596,292 | 8/1971 | Erb | 606/187 |
| 4,751,927 | 6/1988 | Yamada | 606/187 |
| 5,578,054 | 11/1996 | Arnold | 606/187 |

FOREIGN PATENT DOCUMENTS

| | | | |
|---|---|---|---|
| 2666978 | 3/1992 | France | 606/187 |

*Primary Examiner*—Gary Jackson

[57] ABSTRACT

A hemostatic dilator including a top handle extent with an intermediate surgicell extent coupled thereto. The intermediate surgicell has a helix integrally formed along an entire length thereof for allowing the application of a hemostatic agent thereon. Further provided is a lower blade extent for piercing a scalp.

11 Claims, 3 Drawing Sheets

5,797,945

1

HEMOSTATIC DILATOR

BACKGROUND OF THE INVENTION

1. Field of the Invention

The present invention relates to a hemostatic dilator and more particularly pertains to preventing the bleeding of a scalp which results from the piercing thereof prior to the installation of a hair graft.

2. Description of the Prior Art

The use of hemostatic agents and applicators is known in the prior art. More specifically, hemostatic agents and applicators heretofore devised and utilized for the purpose of preventing bleeding are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 5,342,384 to Sugarbaker; U.S. Pat. No. 5,391,178 to Yapor; U.S. Pat. No. 5,312,360 to Behl; U.S. Pat. No. 4,018,230 to Ochiai et al; U.S. Pat. No. 5,222,974 to Kensey et al.; U.S. Pat. No. 5,192,302 to Kensey.

In this respect, the hemostatic dilator according to the present invention substantially departs from the conventional concepts and designs of the prior art, and in so doing provides an apparatus primarily developed for the purpose of preventing the bleeding of a scalp which results from the piercing thereof prior to the installation of a hair graft.

Therefore, it can be appreciated that there exists a continuing need for a new and improved hemostatic dilator which can be used for preventing the bleeding of a scalp which results from the piercing thereof prior to the installation of a hair graft. In this regard, the present invention substantially fulfills this need.

SUMMARY OF THE INVENTION

In view of the foregoing disadvantages inherent in the known types of hemostatic agents and applicators now present in the prior art, the present invention provides an improved hemostatic dilator. As such, the general purpose of the present invention, which will be described subsequently in greater detail, is to provide a new and improved hemostatic dilator which has all the advantages of the prior art and none of the disadvantages.

To attain this, the present invention essentially comprises a top handle extent defining approximately 64% the entire length of the hemostatic dilator. The top extent has an elongated cylindrical configuration with a plurality of intersecting grooves formed in an entire outer surface thereof thereby defining a gripping surface. As shown in FIGS. 1–2, an intermediate surgicell extent is included defining approximately 32% the entire length of the hemostatic dilator. The intermediate extent has a generally cylindrical configuration. A helix is integrally formed along an entire length thereof. Such helix defines a serpentinely situated groove adapted to contain a hemostatic agent. It should be noted that the diameter of the intermediate surgicell extent approximately 20 mm. As shown in the Figures, the top handle extent and the intermediate surgicell extent are maintained in a coaxial relationship. Formed between the top handle extent and the intermediate surgicell extent is a stopper segment. The stopper portion is defined by a pair of frusto-conical segments. A large base of each segment is integrally formed to the other wherein an interconnection of the segment defines a protrusion extending radially outwardly from the outer surface of the top handle extent and the intermediate surgicell extent. Further provided is a bottom blade extent with a flat triangular configuration. The bottom blade extent has a conical configuration having a base integrally formed on a lower end of the intermediate surgicell extent and a sharp cutting tip.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved hemostatic dilator which has all the advantages of the prior art hemostatic agents and applicators and none of the disadvantages.

It is another object of the present invention to provide a new and improved hemostatic dilator which may be easily and efficiently manufactured and marketed.

It is a further object of the present invention to provide a new and improved hemostatic dilator which is of a durable and reliable construction.

An even further object of the present invention is to provide a new and improved hemostatic dilator which is susceptible of a low cost of manufacture with regard to both materials and labor, and which accordingly is then susceptible of low prices of sale to the consuming public, thereby making such hemostatic dilator economically available to the buying public.

Still yet another object of the present invention is to provide a new and improved hemostatic dilator which provides in the apparatuses and methods of the prior art some of the advantages thereof, while simultaneously overcoming some of the disadvantages normally associated therewith.

Still another object of the present invention is to prevent the bleeding of a scalp which results from the piercing thereof prior to the installation of a hair graft.

Lastly, it is an object of the present invention to provide a new and improved hemostatic dilator including a top handle extent with an intermediate surgicell extent coupled thereto. The intermediate surgicell has a helix integrally formed along an entire length thereof for allowing the application of a hemostatic agent thereon. Further provided is a lower blade extent for piercing a scalp.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
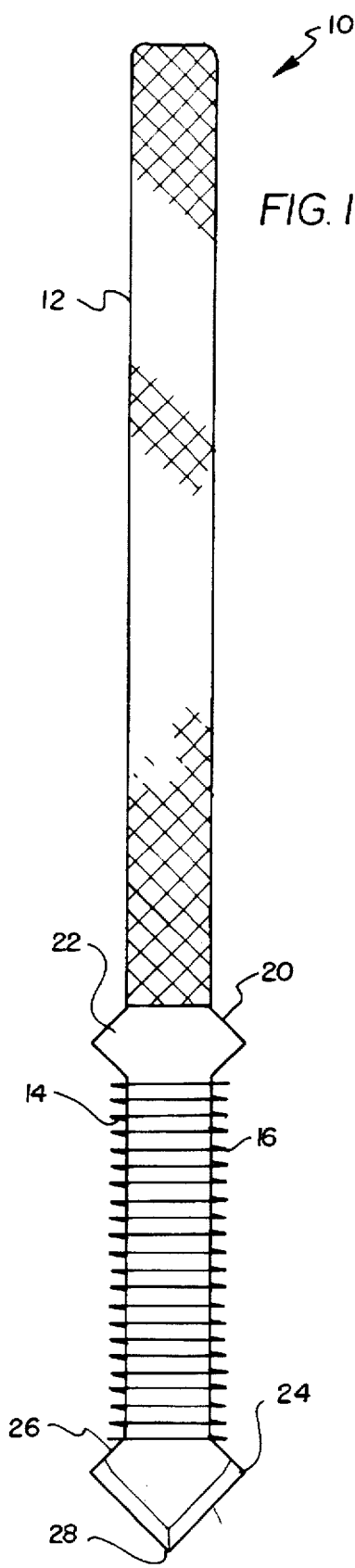
FIG. 1 is an illustration of the preferred embodiment of the hemostatic dilator constructed in accordance with the principles of the present invention.

With reference now to the drawings, and in particular to FIG. 1 thereof, a new and improved hemostatic dilator embodying the principles and concepts of the present invention and generally designated by the reference numeral 10 will be described.

The present invention, the new and improved hemostatic dilator, is comprised of a plurality of components. Such components in their broadest context include a top handle extent, intermediate surgicell extent, and a bottom blade extent. Such components are individually configured and correlated with respect to each other so as to attain the desired objective.

More specifically, it will be noted that the system 10 of the first embodiment of the present invention includes device with a length of approximately 4.7 cm. Such device includes a top handle extent 12 with length of approximately 3 cm thereby defining approximately 64% the entire length of the hemostatic dilator. The top extent has an elongated cylindrical configuration with a plurality of intersecting grooves 14 formed in an entire outer surface thereof thereby defining a gripping surface.

Figure 2:
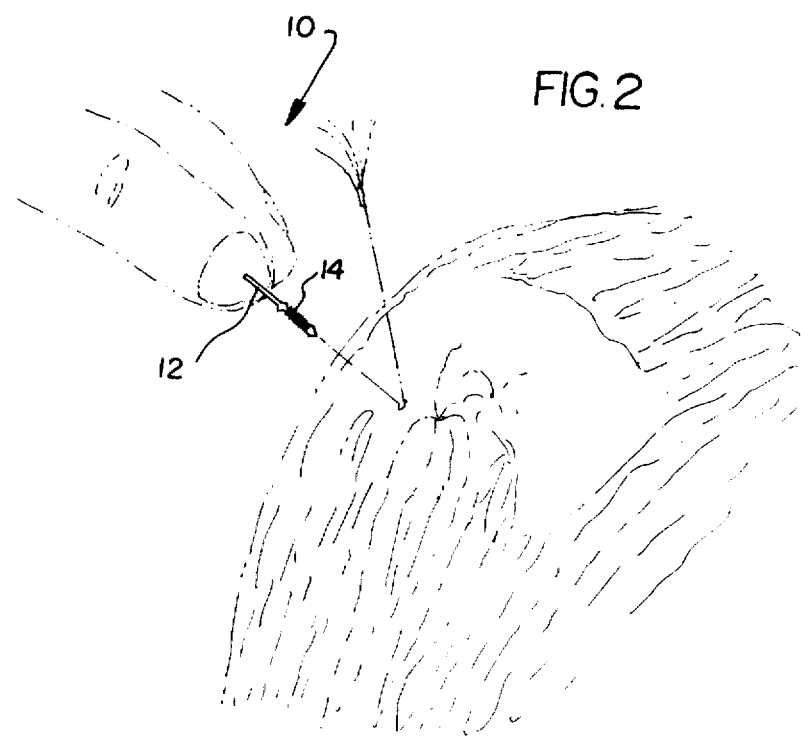
FIG. 2 is an illustration of the present invention in use.
Figure 3:
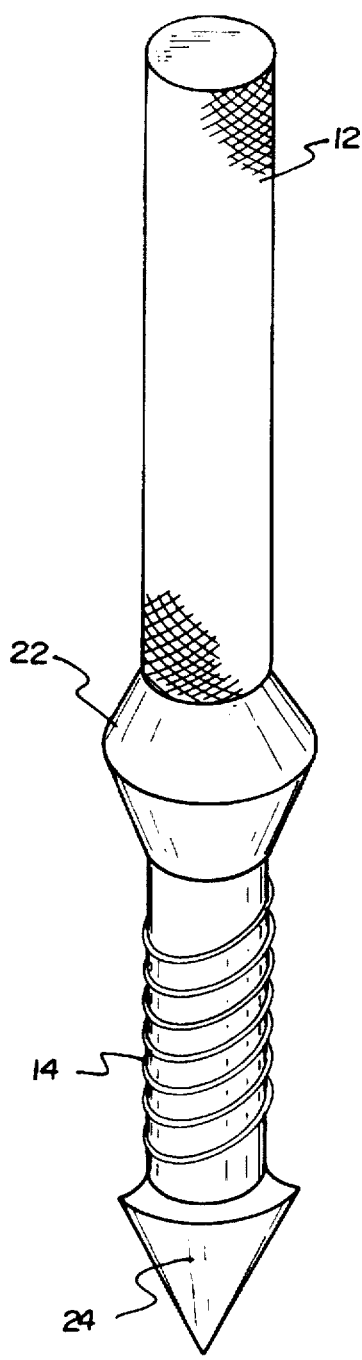
FIG. 3 is a perspective view of the present invention.

As shown in FIGS. 1-2, an intermediate surgicell extent 14 is included with a length of approximately 1.5 cm thus defining approximately 32% the entire length of the hemostatic dilator. The intermediate extent has a generally cylindrical configuration. A helix 16 is integrally formed along an entire length thereof. Such helix defines a serpentinely situated groove adapted to contain a hemostatic agent. It should be noted that the diameter of the intermediate surgicell extent is approximately 20 mm. As shown in the Figures, the top handle extent and the intermediate surgicell extent are maintained in a coaxial relationship.

In an alternate embodiment, the device has a total length of approximately 4.2 cm and the length of the top handle extent is 3 cm thereby defining approximately 71% the length of the device. Also in the alternate embodiment, the intermediate extent is approximately 1 cm thereby defining 24% of the top. It should be further noted that the diameter of the intermediate extent of the alternate embodiment is only 10 mm.

Formed between the top handle extent and the intermediate surgicell extent is a stopper segment 20. The stopper portion is defined by a pair of frusto-conical segments 22. A large base of each segment is integrally formed to the other wherein an interconnection of the segment defines a protrusion extending radially outwardly from the outer surface of the top handle extent and the intermediate surgicell extent. In use, the stopper functions to prevent the insertion of surgicell within a scalp past a certain distance.

Further provided is a bottom blade extent 24 with a conical configuration. The bottom blade extent has a base 26 integrally formed on a lower end of the intermediate surgicell extent and a sharp cutting tip 28.

In use, a hemostatic agent may be applied about the intermediate surgicell extent and the top handle extent may be utilized to facilitate the piercing of a scalp with the bottom blade extent. During the piercing, the hemostatic agent is applied to the scalp thereby precluding bleeding. After the removal of the present invention, an aperture is created within the scalp which is ideal for the placement of a hair graft therein.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by letters patent of the United states is as follows:

1. A new and improved hemostatic dilator comprising, in combination:

a top handle extent defining approximately 64% the entire length of the hemostatic dilator, the top extent having an elongated cylindrical configuration with a plurality of intersecting grooves formed in an entire outer surface thereof thereby defining a gripping surface;

an intermediate extent defining approximately 32% the entire length of the hemostatic dilator, the intermediate extent having a generally cylindrical configuration with a helix integrally formed along an entire length thereof, the diameter of the intermediate extent being 20 mm;

a stopper segment integrally formed between the top handle extent and the intermediate extent such that the top handle extent and the intermediate extent are maintained in a coaxial relationship, the stopper portion being defined by a pair of frusto-conical segments with a large base of each segment integrally formed together wherein an interconnection of the segment defines a protrusion extending radially outwardly from the outer surface of the top handle extent and the intermediate extent; and a bottom blade extent with a conical configuration having a base integrally formed on a lower end of the intermediate extent and a sharp cutting tip;

whereby the hemostatic agent may be applied about the intermediate extent and the top handle extent may be utilized to facilitate the piercing of a scalp with the bottom blade extent such that the hemostatic agent is applied to the area being pierced thereby precluding bleeding.

2. A hemostatic dilator comprising:

a top handle means;

an intermediate extent coupled to the handle means having a helix integrally formed along an entire length thereof for allowing the application of a hemostatic agent thereon; and means for piecing a scalp;

whereby the hemostatic agent may be applied about the intermediate extent and the top handle means may be utilized to facilitate the piercing of the scalp with the blade means such that the hemostatic agent is applied to the area being pierced thereby precluding bleeding.

3. A hemostatic dilator as set forth in claim 2 and further including a stopper segment integrally formed between the top handle means and the intermediate extent such that the top handle means and the intermediate extent are maintained in a coaxial relationship, the stopper portion being defined by a pair of frusto-conical segments with a large base of each segment integrally formed together wherein an interconnection of the segment defines a protrusion extending radially outwardly from the outer surface of the top handle means and the intermediate extent.

4. A hemostatic dilator as set forth in claim 2 wherein the top handle means has an elongated cylindrical configuration with a plurality of intersecting grooves formed in an entire outer surface thereof thereby defining a gripping surface.

5. A hemostatic dilator as set forth in claim 2 wherein the blade means has a conical configuration having a base integrally formed on a lower end of the intermediate extent and a sharp cutting tip.

6. A hemostatic dilator as set forth in claim 2 wherein the diameter of the intermediate extent is approximately 20 mm.

7. A hemostatic dilator as set forth in claim 2 wherein the intermediate extent defines approximately 32% the entire length of the hemostatic dilator.

8. A hemostatic dilator as set forth in claim 2 wherein the top handle means defines approximately 64% the entire length of the hemostatic dilator.

9. A hemostatic dilator as set forth in claim 2 wherein the diameter of the intermediate extent is approximately 10 mm.

10. A hemostatic dilator as set forth in claim 2 wherein the intermediate extent defines approximately 24% the entire length of the hemostatic dilator.

11. A hemostatic dilator as set forth in claim 2 wherein the top handle means defines approximately 71% the entire length of the hemostatic dilator.

* * * * *